United States Patent
Smith et al.

(10) Patent No.: US 6,923,065 B2
(45) Date of Patent: *Aug. 2, 2005

(54) APPARATUS FOR TESTING ARAMID FIBER ELEVATOR CABLES

(75) Inventors: Rory Smith, El Cajon, CA (US); Robert H. Sweet, Lakeside, CA (US); James Nickerson, Spring Valley, CA (US); Michael A. Palazzola, San Diego, CA (US); Randall Parrish, Pine Valley, CA (US)

(73) Assignee: Thyssen Elevator Capital Corp., Whittier, CA (US)

( * ) Notice: Subject to any disclaimer, the term of this patent is extended or adjusted under 35 U.S.C. 154(b) by 15 days.

This patent is subject to a terminal disclaimer.

(21) Appl. No.: 10/661,257

(22) Filed: Sep. 12, 2003

(65) Prior Publication Data

US 2004/0099062 A1 May 27, 2004

Related U.S. Application Data

(63) Continuation-in-part of application No. 09/953,689, filed on Sep. 17, 2001, now Pat. No. 6,662,660.

(51) Int. Cl.[7] .......................... G01N 29/00; G01H 5/00; G01R 31/08
(52) U.S. Cl. ............................ 73/597; 73/602; 324/535
(58) Field of Search ....................... 73/597, 602, 598, 73/643, 620, 632; 324/535, 539, 542; 367/3, 127

(56) References Cited

U.S. PATENT DOCUMENTS

| | | | |
|---|---|---|---|
| 4,295,212 A | 10/1981 | Swenson .................... 368/20 |
| 4,445,593 A | 5/1984 | Coleman et al. ............ 187/413 |
| 4,622,853 A | 11/1986 | Leugers ....................... 73/597 |
| 4,947,851 A | 8/1990 | Sarvazyan et al. ..... 128/660.02 |
| 4,979,125 A * | 12/1990 | Kwun et al. .................. 702/35 |
| 5,456,113 A * | 10/1995 | Kwun et al. .................. 73/587 |
| 5,741,971 A * | 4/1998 | Lacy ........................... 73/597 |
| 5,834,942 A | 11/1998 | De Angelis ................. 324/522 |
| 6,164,137 A * | 12/2000 | Hancock et al. .............. 73/643 |
| 6,176,132 B1 * | 1/2001 | MacLauchlan ............ 73/290 V |
| 6,236,218 B1 | 5/2001 | Johansson et al. .......... 324/536 |
| 6,276,209 B1 * | 8/2001 | Schafer et al. ................ 73/597 |
| 6,450,036 B1 * | 9/2002 | Ashida et al. ................ 73/584 |
| 6,662,660 B2 * | 12/2003 | Smith .......................... 73/597 |

OTHER PUBLICATIONS

M. Ferreira, T.M. Lam, V. Koncar, Y. Delvael, "Non–destructive testing of Polyaramide Cables by Longitudinal Wave Propagation: Study of the Dynamic Modulus", Polymer Science Engineering, vol. 40, No. 7, pp. 1628–1634.

* cited by examiner

Primary Examiner—Hezron Williams
Assistant Examiner—Jacques M. Saint-Surin
(74) Attorney, Agent, or Firm—Frost Brown Todd LLC

(57) ABSTRACT

An apparatus and method for inspecting and calculating the residual strength of an aramid fiber rope driving an elevator to determine when such rope is in need of replacement. The apparatus comprises a transmitter for introducing an acoustic wave that will travel along the aramid fiber rope and a plurality of receivers for receiving the acoustic wave after its has traversed a designated section of the rope. The transmitter and receiver provide signals indicating the times the wave was sent by the transmitter and thereafter received by the receiver. From these signals, a program calculates the wave velocity, and the modulus and residual strength of the aramid rope.

18 Claims, 4 Drawing Sheets

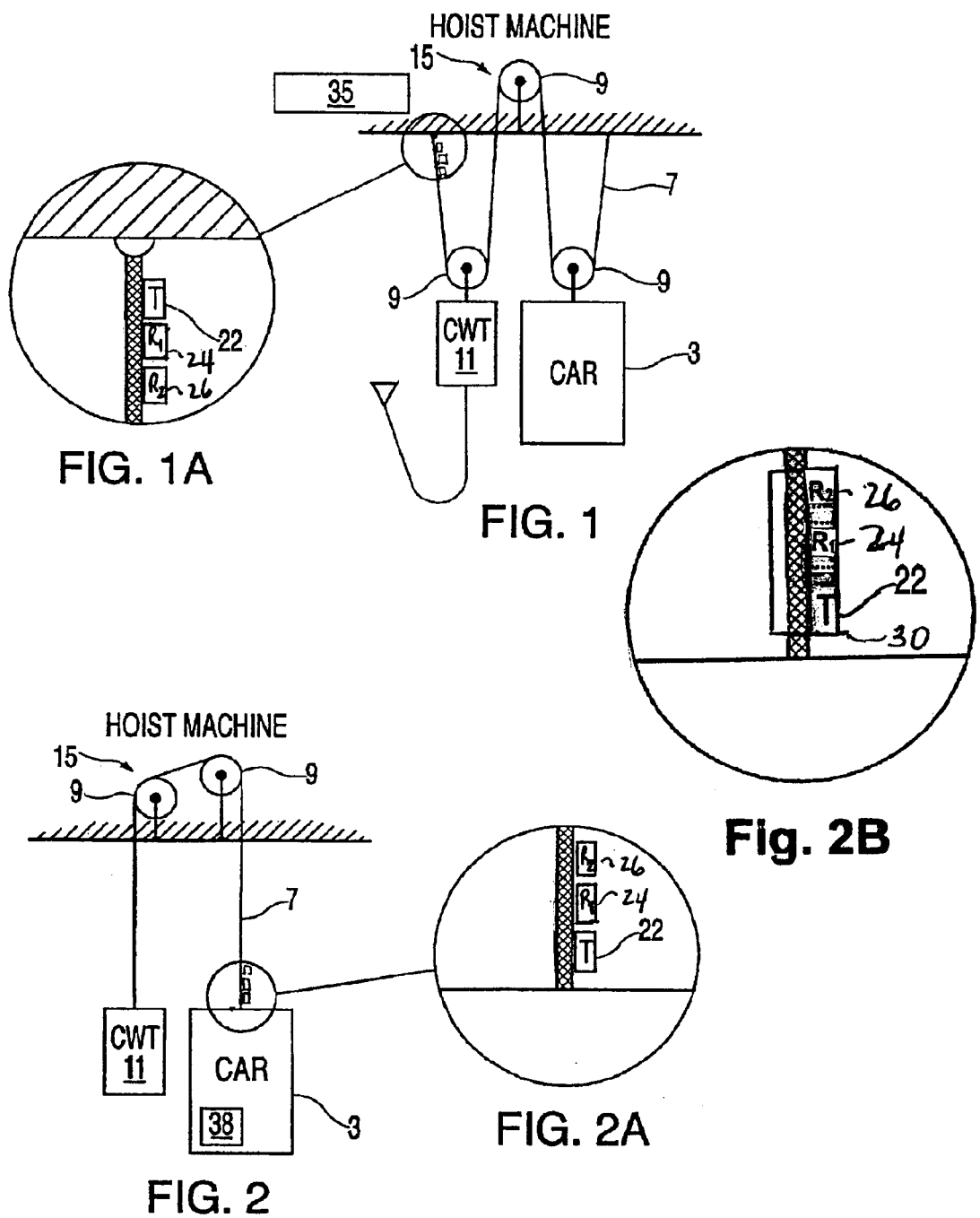

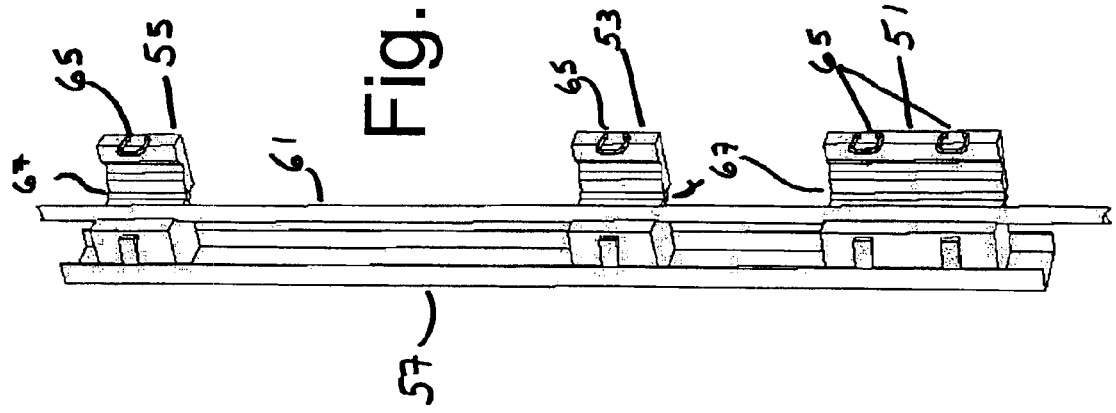
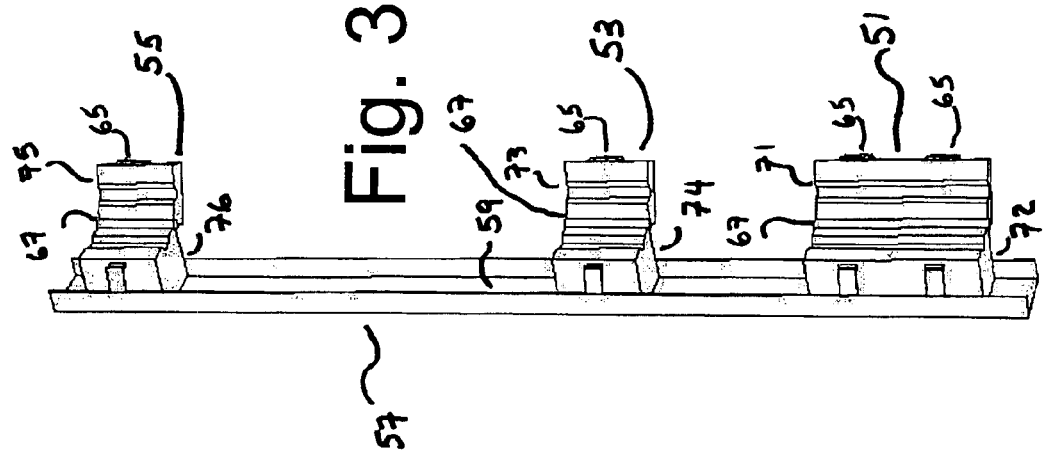

APPARATUS FOR TESTING ARAMID FIBER ELEVATOR CABLES

This application is a continuation-in-part of U.S. application Ser. No. 09/953,689, filed Sep. 17, 2001 now U.S. Pat. No. 6,662,660, which is hereby incorporated by reference in its entirety.

FIELD OF THE INVENTION

The present invention relates to elevator systems. More specifically, the invention relates to an apparatus and method for testing aramid fiber ropes used in elevator systems in order to determine when such ropes have reached the end of their useful lifetimes and are in need of replacement.

BACKGROUND OF THE INVENTION

Traditional steel elevator ropes can be visually inspected for wear. The individual wires will break and these breaks can be easily observed. Aramid fiber elevator ropes are typically covered with a protective sheathing which makes visual inspection difficult. Even if the ropes were not sheathed, it would still be difficult to determine the proper time to replace the ropes because the appearance of the fibers is almost identical whether the fibers are new or in need of replacement.

Prior art ropes have resorted to placing conductive fibers within the ropes so that the fibers can be monitored by electrical means. For example, U.S. Pat. No. 5,834,942 to De Angelis, issued Nov. 10, 1998, discloses an apparatus for determining when a synthetic fiber cable for an elevator is ready for replacement. The apparatus includes a voltage detection device for detecting a voltage in at least one carbon fiber of the synthetic fiber cable and at least one threshold device for determining when the detected voltage exceeds a predetermined voltage threshold. The detected voltage depends upon the integrity of that portion of the synthetic cable in which the carbon fibers are located. Exceeding the predetermined voltage threshold is indicative of a failure of that portion of the cable. This apparatus, therefore, may not be suitable for synthetic cables that are not readily conductive.

It has been shown that the elastic properties of aramid materials can be determined from the measurement of wave propagation through the material. (See M. Ferreira et al., "Nondestructive Testing of Polyaramide Cables by Longitudinal Wave Propagation: Study of the Dynamic Modulus", Polymer Engineering and Science, Vol. 40, No. 7, July 2000, which is hereby incorporated by reference in its entirety.) In particular, it has been observed that polyaramid cables at different states of fatigue have their own speed of longitudinal propagation of acoustic waves. It has been observed that longitudinal waves travel through aramid fiber ropes in accordance with the following formula:

$$V^2 = \frac{E}{\rho} \quad \text{(Equation 1)}$$

where V=velocity of wave propagation, E=dynamic or sonic modulus, and ρ=density. Since the tensile modulus and acoustic modulus both change at the same rate with fatigue, it is possible to calculate the tensile modulus from the observed values of wave propagation. Plotting E (modulus) against Fr (residual strength), it was found that E=f (Fr). In other words, a quantifiable relationship exists between modulus (determined from velocity) and residual strength.

A similar relationship between modulus and residual strength may be determined for aramid ropes used in elevator systems. The relationship will vary based on the particular aramid material used and the dimensions of the rope. Once the relationship is determined, it will be possible to extrapolate the residual strength of the rope from determinations of modulus. This has not heretofore been achieved for elevator systems.

Thus, an objective of the present invention is to provide an apparatus and method for inspecting aramid fiber elevator ropes which are under tension, and for calculating the residual strength of such ropes to determine when they need replacement.

SUMMARY OF THE INVENTION

According to an embodiment of the invention, an apparatus is provided for inspecting and calculating the residual strength of an aramid fiber suspension rope driving an elevator. The apparatus comprises a housing, which comprises (a) a transmitter for introducing an acoustic wave along the aramid fiber rope; (b) a first receiver for receiving the acoustic wave traveling along the aramid fiber rope and providing a first signal indicative of the time when the first receiver has received the acoustic wave; and (c) a second receiver for receiving the acoustic wave traveling along the aramid fiber rope and providing a second signal indicative of the time when the second receiver has received the acoustic wave. The apparatus comprises processing means for processing the first and second signals to calculate the residual strength of the rope.

The processing means may include a control system which is connected to the transmitter and the receivers. The control system may have a program and associated algorithms for processing the time between the first and second signals, in connection with the distance between the first and second receivers, to calculate (i) the velocity of the acoustic wave; (ii) the modulus of the rope; and (iii) the residual strength of the rope.

The housing of the apparatus may be removable from the transmitter and the first and second receivers prior to data collection, and data collected with only the transmitter and two receivers positioned on the rope. Alternatively, the transmitter and first and second receivers may be securely mounted to or within the housing. In such an embodiment, data is generated with the housing, and thereby the transmitter and receivers, disposed on the aramid rope.

The apparatus may comprise alignment means for aligning the transmitter and first and second receivers on the aramid rope. The alignment means facilitates positioning each of the transmitter and first and second receivers at a predetermined position or distance apart along the aramid fiber rope. The alignment means may be removable from or firmly affixed to the apparatus. In an embodiment of the invention, the alignment means is a jig which receives the transmitter and receivers, and is removable from the transmitter and receivers prior to data collection.

The transmitter and the first and second receivers may comprise clamping means for maintaining each of the transmitter and the receivers in acoustical contact with the aramid fiber rope during data collection. The position of any one or more of the transmitter and the first and second receivers will typically be fixable along the aramid fiber rope.

The transmitter may introduce the acoustic wave along the aramid fiber rope in any convenient manner. In an embodiment of the invention, the acoustic wave is introduced along the aramid fiber rope by striking a surface of the transmitter. For example, the transmitter may comprise a solenoid having a pin which strikes an interior surface of the transmitter. The resultant vibrational signal is then be transmitted along the rope and detected by the two receivers.

The first receiver, the second receiver, or both, may comprise a vibration sensor for sensing the vibration caused by the acoustic wave introduced along the rope by the transmitter. The vibration sensor may be any type of sensor capable of detecting the acoustic waves. In an embodiment of the invention, the vibration sensor is a piezoelectric vibration sensor. The piezoelectric vibration sensor may comprise a vibratory mass member for detecting the acoustic wave.

The apparatus may comprise signal amplification circuitry for amplifying signals generated by the acoustic wave traveling along the aramid fiber rope. The apparatus may also comprise signal filtering circuitry for filtering noise from signals generated by the acoustic wave traveling along the rope.

Although an embodiment of the apparatus has been described as including one transmitter and two receivers, the apparatus may comprise any number of additional transmitters for introducing additional acoustic waves along the aramid rope. The apparatus may also comprise any number of additional receivers for receiving the acoustic wave traveling along the aramid fiber rope and for providing corresponding signals indicative of the time when the additional receivers have received the acoustic wave.

The first and second receiver will generally contain substantially similar electronic circuitry and function in the same manner, although in alternative embodiments of the invention, the receivers may not be identical. The position of the transmitter and first and receivers on the rope will depend upon the particular characteristics of the elevator system and aramid rope. The second receiver will generally be positioned on the rope further from the transmitter than the first receiver.

According to another aspect of the present invention, a method is provided for inspecting and calculating the residual strength of an aramid fiber rope driving an elevator to determine when the rope is in need of replacement. The method comprises providing a transmitter along the aramid fiber rope for introducing an acoustic wave in the rope, and first and second receivers along the aramid fiber rope.

The first receiver is capable of detecting the acoustic wave traveling in the rope and providing a first signal indicative of the time when the first receiver has received the wave, and the second receiver is capable of detecting the acoustic wave traveling in the rope and providing a second signal indicative of the time when the second receiver has received the wave. The second receiver will generally be positioned on the rope further from the transmitter than the first receiver.

The method comprises introducing an acoustic wave along the rope with the transmitter, and determining the time between the first signal generated by the first receiver and the second signal generated by the second receiver. The time between the two signals is used to determine the velocity of the acoustic wave in the rope and to calculate the modulus and residual strength of the rope.

BRIEF DESCRIPTION OF THE FIGURES

FIG. 1 shows an embodiment of the invention embodied in a first elevator system in which one transmitter and two receivers are disposed on an aramid fiber rope.

FIG. 1A shows an enlarged view of the transmitter and receivers illustrated in FIG. 1.

FIG. 2 shows an embodiment of the invention in a second elevator system.

FIG. 2A shows an enlarged view of the transmitter and receivers illustrated in FIG. 2.

FIG. 2B shows an embodiment of the invention wherein the transmitter and receivers are disposed on an aramid rope, and are located within a housing.

FIG. 3 shows an embodiment of the invention wherein a transmitter and two receivers are aligned in a jig and are ready to receive an elevator rope.

FIG. 4 shows the embodiment of FIG. 3 in which the transmitter and receivers are in an open position and have been placed around an aramid elevator rope.

DETAILED DESCRIPTION OF THE INVENTION

Figure 6:
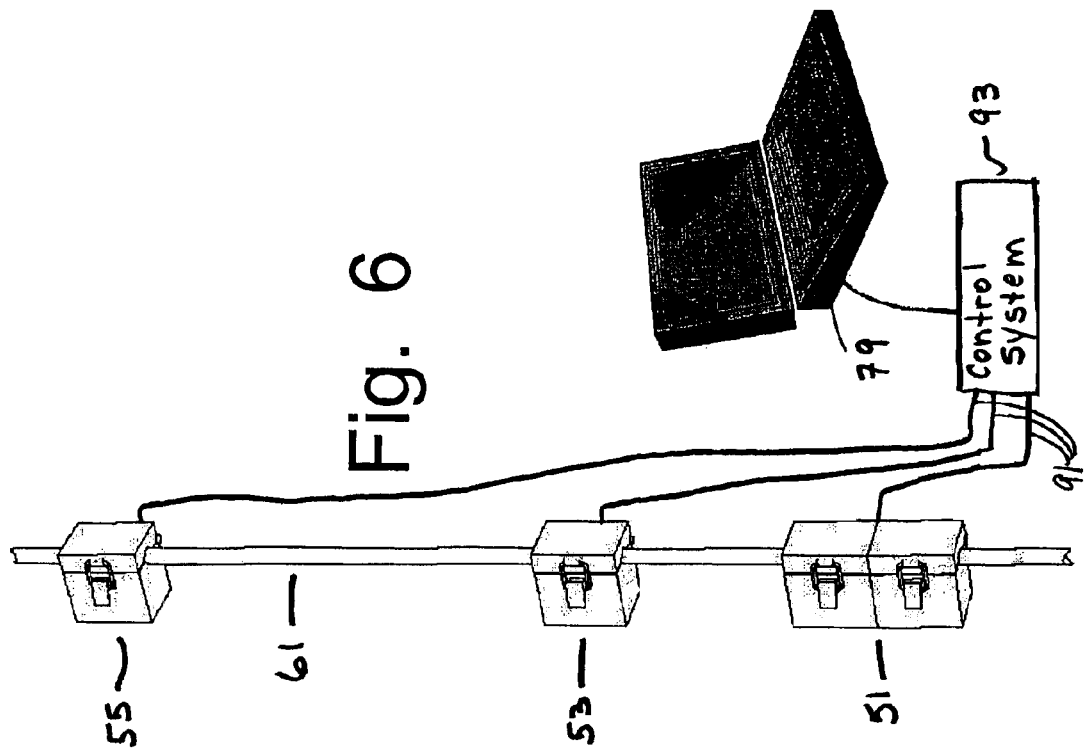
FIG. 6 shows an embodiment of the invention wherein the transmitter and receivers are connected to a control system of a computer.

The claimed invention will now be described with reference to the figures, wherein like numerals correspond to like elements. For ease of discussion, the expression "sensor" will collectively describe any one or more of the transmitter and/or receiver units. For clarity of illustration, certain elements such as a housing or wires have been omitted from several of the FIGS.

FIG. 1 shows an embodiment of the invention which has been incorporated into an elevator system. The elevator system includes an elevator car 3 suspended by an aramid fiber rope 7. The aramid fiber rope 7 rides over one or more sheaves 9 and is also coupled to a counterweight 11 in order to balance the system. A hoist machine 15, which includes one of the sheaves 9, drives the rope in either of two directions in order to raise and lower the elevator car 3. The aramid fiber rope 7 will typically be covered with a sheathing to increase traction.

The apparatus according to this embodiment of the invention is incorporated into the system as follows. Referring to enlarged views of FIGS. 1A and 2A, a transmitter 22 and two receivers 24 and 26, all of which are constructed from piezoelectronic sonic sensors, are connected to the aramid fiber rope 7 which is maintained under tension. Transmitter 22 contains components that can introduce an acoustic wave along the aramid fiber rope 7. The transmitter 22 may be configured to generate signals that indicate the time the acoustic wave was initially introduced within the rope 7, and receivers 24 and 26 generate first and second signals, respectively, which indicate the time when the acoustic wave is thereafter received by the receivers 24 and 26.

A means for processing the first and second signals to calculate the residual strength of the rope 7 maintained under tension is provided. In particular, the invention provides an elevator control system 35 that is connected to both the transmitter 22 and receivers 24 and 26. The control system 35 has a program containing the appropriate algorithms for calculating the velocity of the wave based on the first and second signals. The control system 35 and program may be located in the machine room (as in FIG. 1). In addition, as shown in FIG. 2, the elevator car 3 may contain an interface 38 that receives signals from the transmitter and receivers and sends those signals to the control system 35. The program within the control system 35 calculates the modulus of the rope 7, and in turn determines the residual strength of the rope 7 from a stored equation representing residual strength as a function of modulus.

The sensors 22, 24, 26 of the apparatus may be separately disposable onto the aramid rope. Alternatively, the sensors can be mounted within a housing 30 (as in FIG. 2B). In such an embodiment, the rope is placed in the housing, and the need to affix each individual sensor to the rope is avoided. A single housing 30 can comprise all sensors, or separate housings (not illustrated) can be used for each sensor.

In certain embodiments of the invention, the apparatus can be permanently or semi-permanently disposed onto the aramid rope. Alternatively, the apparatus can be disposed onto the rope during a testing period, and removed when testing has concluded.

When the calculated residual strength drops below a predetermined threshold, the control system 35 will provide the appropriate notification that the aramid rope 7 needs replacement. If desired, the control system 35 may also be programmed to shut down the elevator when the residual strength of the aramid rope 7 falls below the threshold. Values for the residual strength may be determined periodically and automatically stored in the control system's memory for use in predicting rope life. This is an important advantage because the rope may be tested and the residual strength determined while the rope remains installed in the elevator system. In particular, the apparatus of the invention may continuously test the residual strength of the rope, and may do so by testing various portions of the rope while the elevator is in operation. Generally, the cab will be stopped during testing to minimize acoustic vibration in the rope which may interfere with testing.

By running tests on portions of the ropes while the elevator car is located in various places within the system, the apparatus of the invention is ultimately able to test the entire length of the rope. One particular option in this regard, is for the apparatus to test various successive portions of the rope incrementally to provide an overall evaluation of the rope. Another option may be to test portions randomly.

In another embodiment of the invention, the apparatus may comprise means for positioning the transmitter and receivers onto the aramid fiber rope. This positioning means may take many forms, such as a jig illustrated in FIGS. 3–5. For clarity, circuitry and wiring diagrams have been omitted from FIGS. 3–5.

Figure 5:
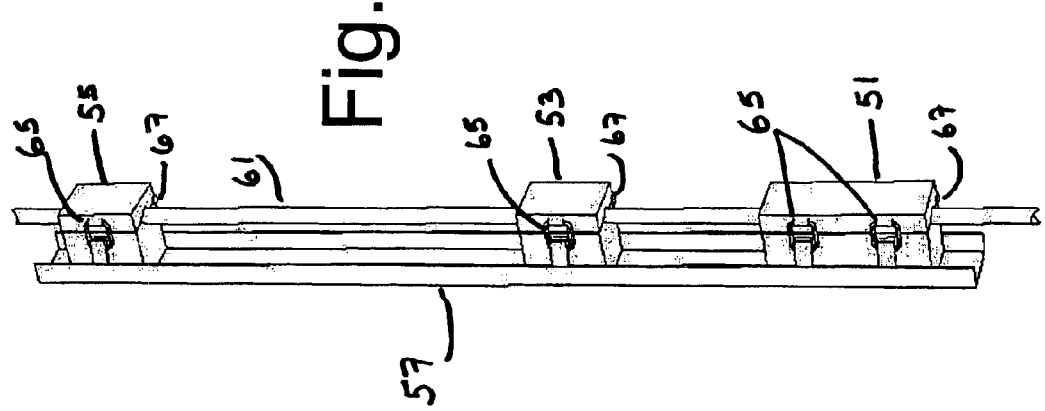
FIG. 5 shows an the embodiment of FIG. 4 in which the transmitter and receivers have been secured around an aramid rope.

In FIGS. 3–5, the apparatus comprises a jig 57 for facilitating the positioning of the transmitter 51 and two receivers 53 and 55 on the aramid rope. That is, the transmitter 51 and receivers 53 and 55 can be placed in the jig in a predetermined orientation, location, and distance apart, and the jig 57 maintains the transmitter 51 and receivers 53 and 55 in that alignment. The jig 57 includes a channel 59, in which the transmitter 51 and receivers 53 and 55 are retained by a friction fit, and from which the transmitter 51 and receivers 53 and 55 are readily releasable. The friction fit permits the transmitter 51 and receivers 53 and 55 to be readily moved closer or further apart, within or outside a housing, as circumstances require.

In other embodiments of the invention, alternative means are provided for adjusting the position of the transmitter and receivers on the rope. For example, a placement guide may be used in place of a jig. The alignment means may or may not be removed from the sensors or housing prior to data collection.

In FIG. 3, the transmitter 51 and receivers 53 and 55 are shown in an opened state, and are ready to receive the aramid rope. In FIG. 4, aramid rope 61 has been laid within the transmitter 51 and receivers 53 and 55. The rope will normally be under tension and installed in a vertical orientation in an elevator system. In FIG. 5, the transmitter and receivers have been closed and fastened about the rope. After the transmitter 51 and receivers 53 and 55 are securely fastened in place about the rope 61, the apparatus is ready for use.

In the embodiment illustrated in the figures, the transmitter 51 is a single unit which comprises a first section 71 and a second section 72, which are connected by a hinge 65. Similarly, the receivers 53 and 55 comprise respective first sections 73 and 75, and second sections 74 and 76 connected by hinges 65. The first and second sections of the sensors each contain semicircular areas which are structurally configured to closely fit or mate around the aramid rope, and thereby permit optimal acoustic contact of the sensors with the rope.

The housing, or each individual transmitter and receiver of the apparatus, can comprise a fastener for removably maintaining these sensors units affixed to the aramid rope. The fastener will generally provide a constant clamping force on the sensors to the rope to restrict movement and thereby facilitate data reproducibility. A latch 65 and hinge 67 mechanism is illustrated in the FIGS. as one example of a fastener to keep the sensors securely but removably disposed on and in acoustic contact with the rope. In other embodiments, other mechanisms such as a clamp, couple, or brace, can be used as fasteners.

FIG. 6 shows an electronic connection arrangement in an alternate embodiment of the invention. Each sensor 51, 53, 55 is attached by a wire 91 to a control system 93. The control system 93 contains the electronic logic and circuitry necessary to generate, collect and process the data prepared through the function of the apparatus. The control system 93 can be any custom-designed or commercially available hardware and/or software product. Although the control system 93 is illustrated as an external standalone hardware item, it may also be an internal computer hardware item such as an electromechanical relay rack or computer circuit board located internally in a computer. The control system 93 may also be a computer controller, a network interface card, a motherboard, or a data acquisition card such as a laptop PCMCIA card. The control system 93 can include a software program used for data acquisition or processing purposes.

The control system 93 is illustrated connected to a computer 79 via wires 91 (omitted from FIGS. 3–5 for clarity). The wires 91 are attached to the sensor units in such a manner that they do not interfere with acoustic wave transmission or data collection. The computer 79 contains the necessary computer logic and circuitry for collection and processing of the data generated by the invention. The computer 79 may be a conventional computer system, and will generally contain conventional components such as an input device, memory, processor, and a display. For ease of transport, the computer 79 may be portable, such as a laptop or pen-based computer or a mobile or wireless handheld device. The software used by the system to collect the data may be a customized version of a commercially available software package, or it may be custom-written.

Although the sensors have been illustrated as connected by a wire to the computer, the sensors may also be in wireless communication with the computer (not illustrated). In this regard, the sensors and computer may communicate and transmit data via infrared light, radio waves, or any other wireless unidirectional or bidirectional means of communication.

Figure 7:
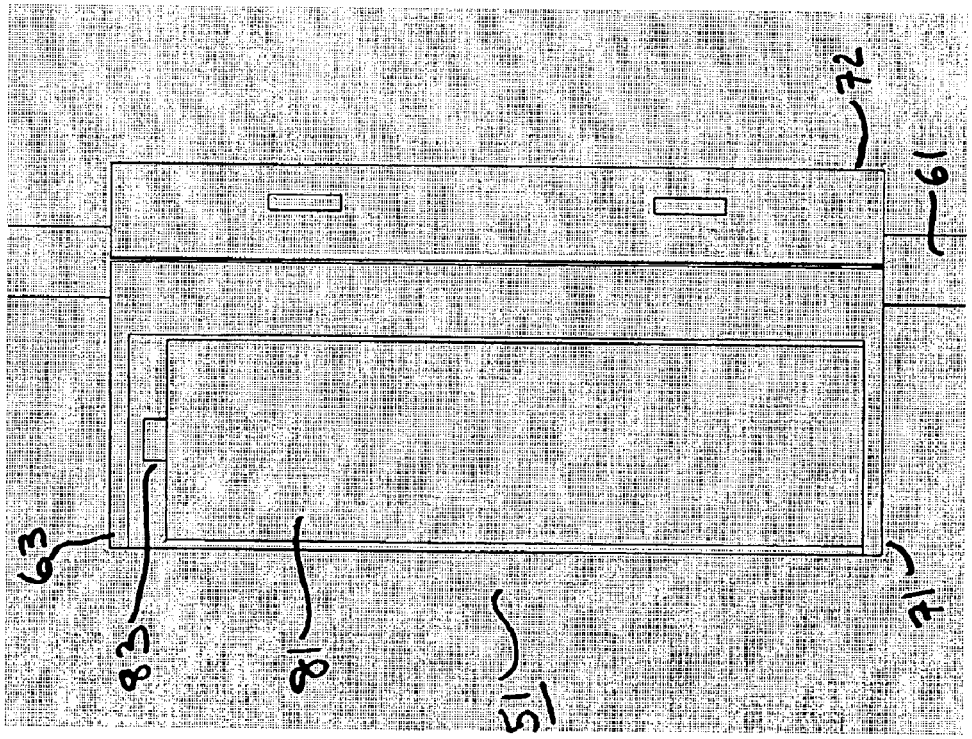
FIG. 7 shows a cross-section of a transmitter according to an embodiment of the invention.

FIG. 7 shows a cross-section of an embodiment of transmitter 51. The transmitter comprises first section 71 and second section 72, both of which are clamped around the rope 61. The transmitter comprises means for imparting an acoustic wave into the rope. The wave may be imparted using any convenient means.

In the embodiment of FIG. 7, the acoustic wave is introduced into the aramid rope by the action of solenoid 81 striking an extended steel plate 63 which is part of transmitter 51. The solenoid 81 has a pin 83, and upon activation of the transmitter 51, the pin 83 extends from the solenoid and strikes the extended steel plate 63 of the transmitter 51. The striking action generates the acoustic wave which enters along the aramid rope, and which is subsequently monitored by detectors 53 and 55 as it moves along the rope 61.

Figure 8:
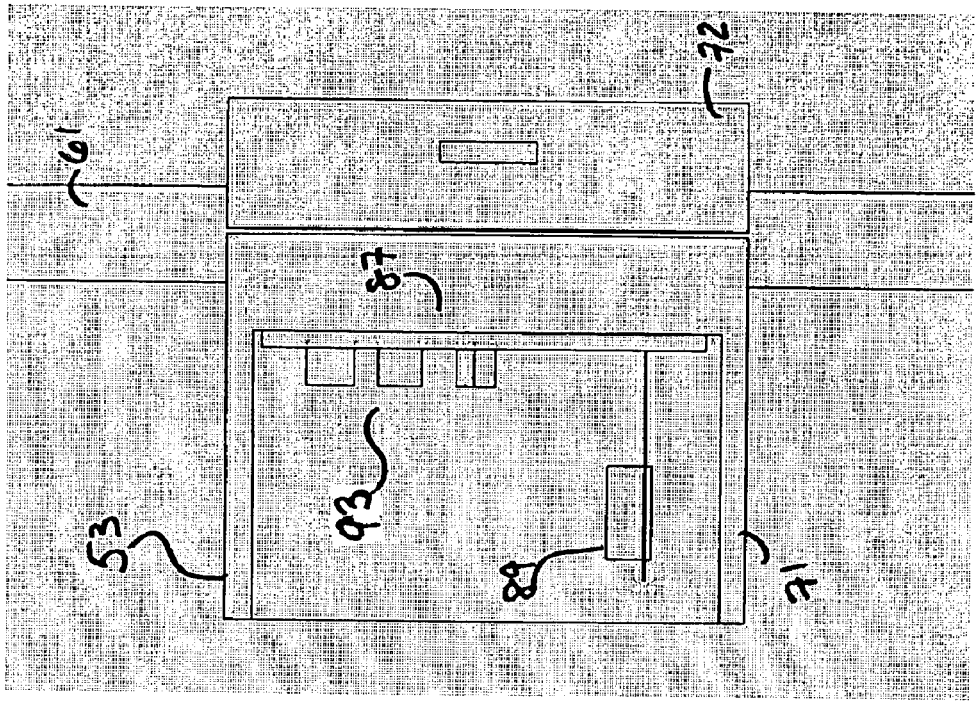
FIG. 8 shows a cross-section of a receiver according to an embodiment of the invention.

FIG. 8 illustrates a cross-section of a receiver according to an embodiment of the invention. The receivers 53 and 55 of the present invention are envisioned to be substantially similar, although in certain embodiments, the receivers may have different configurations. The receiver contains the necessary circuitry and components for detecting the acoustic wave traveling along the aramid rope 61.

In one embodiment of the invention, the receiver 53 comprises a piezoelectric vibration sensor 87, which generates an electronic signal when it detects the acoustic wave passing though the aramid rope 61. The vibrational sensor 87 may contain a vibratory mass member 89 connected to a sheet 93 of piezoelectronic material. In other embodiments of the invention, the transmitter and receiver may be constructed differently.

The distance between the transmitter and the first and second receivers will be variable and will depend upon the particular elevator system. In a typical arrangement, the transmitter and receivers are spaced about 1–2 feet apart from each other. The first sensor will generally be placed on the aramid rope at a closer position to the transmitter than the second sensor. The three sensors do not need to be evenly spaced apart on the rope.

Although the claimed invention has been described as comprising one transmitter and two receivers, in alternative embodiments of the invention, there may be any number of transmitters, any number of receivers, or both. If a plurality of receivers are used, the residual strength data of different sections of the rope can be obtained concurrently. The computer system may also use the additional transmitters, or additional signals provided by additional detectors, in order to refine the quality of, or to increase the number of, data points obtained by the present invention.

An embodiment of a method for inspecting and calculating the residual strength of an aramid fiber rope driving an elevator to determine when the rope is in need of replacement will now be described.

Prior to inspecting an aramid rope using the disclosed apparatus, the elevator system will generally be stopped in order to minimize unintended vibrations to the suspension rope. The transmitter and first and second receivers are disposed on the aramid rope at the desired location, for example, a section of the rope near the ground floor landing, and connected to a computer data system. The transmitter introduces an acoustic wave along the rope, and the acoustic wave is detected by the first and second receivers. The first and second receivers provide respective first and second signals indicative of the time that they have received the acoustic wave. The computer system determines the time between the first and second signals and, using this information and the distance between the first and second sensors, determines the velocity of the acoustic wave in the rope and the residual strength of the rope.

After inspection of that section of the aramid rope has been completed, the apparatus may be moved to another section(s) of the rope, such as another landing, in order to determine the residual strength of the other section(s) of the rope. At the conclusion of testing, the apparatus is removed from the rope. If the residual strength of the aramid rope is deemed to be within desired specifications, the elevator system is returned to normal service. If the residual strength of the rope is less than a predetermined threshold or outside specifications, the rope is deemed to be unsuitable for continued use, and the elevator system is removed from service pending further testing or replacement of the rope.

Numerous modifications and variations of the present invention are possible in light of the above teachings, and therefore, within the scope of the appended claims, the invention may be practiced otherwise than as particularly described.

What is claimed is:

1. An apparatus for inspecting and calculating the residual strength of an aramid fiber suspension rope driving an elevator, the apparatus comprising:

a housing, the housing comprising:

(a) a transmitter for introducing an acoustic wave along the aramid fiber rope;

(b) a first receiver for positioning on a side of the transmitter along the rope and for receiving the acoustic wave traveling along the aramid fiber rope and providing a first signal indicative of the time when the first receiver has received the acoustic wave; and (c) a second receiver for positioning on the side of the transmitter along the rope and for receiving the acoustic wave traveling along the aramid fiber rope and providing a second signal indicative of the time when the second receiver has received the acoustic wave; and processing means for processing the first and second signals to calculate the residual strength of the rope.

2. The apparatus according to claim 1, wherein the means for processing the first and second signals comprises a control system connected to the transmitter and the receivers, the control system having a program and associated algorithms for processing the time between the first and second signals in connection with the distance between the first receiver and the second receiver to calculate (i) the velocity of the wave; (ii) the modulus of the rope; and (iii) the residual strength of the rope.

3. The apparatus according to claim 1, wherein the housing is removable from the transmitter and the first and second receivers prior to data collection.

4. The apparatus according to claim 1, wherein apparatus comprises removable alignment means for aligning the transmitter and first and second receivers on the aramid rope.

5. The apparatus according to claim 4, wherein the alignment means positions one or more of each of the transmitter and first and second receivers at a predetermined position along the aramid fiber rope.

6. The apparatus according to claim 5, wherein the alignment means is a jig.

7. The apparatus according to claim 1, wherein the transmitter and the first and second receivers comprise clamping means for maintaining each of the transmitter and the receivers in acoustical contact with the aramid fiber rope during data collection.

8. The apparatus according to claim 1, wherein the position of any one or more of the transmitter and the first and second receivers are fixable along the aramid fiber rope.

9. The apparatus according to claim 1, wherein the transmitter introduces the acoustic wave along the aramid fiber rope by striking a surface of the transmitter.

10. The apparatus according to claim 9, wherein the transmitter comprises a solenoid which introduces the acoustic wave by striking an interior surface of the transmitter.

11. The apparatus according to claim 1, wherein the first receiver, the second receiver, or both, comprise a vibration sensor for sensing the vibration caused by the acoustic wave introduced along the rope by the transmitter.

12. The apparatus according to claim 11, wherein the vibration sensor is a piezoelectric vibration sensor.

13. The apparatus according to claim 12, wherein the piezoelectric vibration sensor further comprises a vibratory mass member.

14. The apparatus according to claim 1, further comprising signal amplification circuitry for amplifying signals generated by the acoustic wave.

15. The apparatus according to claim 1, further comprising signal filtering circuitry for filtering noise from signals generated by the acoustic wave.

16. The apparatus according to claim 1, further comprising one or more additional receivers for receiving the acoustic wave traveling along the aramid fiber rope and providing one or more corresponding signals indicative of the time when the one or more additional receivers have received the wave.

17. The apparatus according to claim 1, wherein the second receiver is positioned on the rope further from the transmitter than the first receiver.

18. A method for inspecting and calculating the residual strength of an aramid fiber rope driving an elevator to determine when the rope is in need of replacement, the method comprising:
  (a) providing a transmitter along the aramid fiber rope for introducing an acoustic wave along the rope;
  (b) providing a first receiver along the aramid fiber rope, wherein the first receiver is capable of detecting the acoustic wave traveling in the rope and providing a first signal indicative of the time when the first receiver has received the wave;
  (c) providing a second receiver along the aramid fiber rope, wherein the second receiver is capable of detecting the acoustic wave traveling in the rope and providing a second signal indicative of the time when the second receiver has received the wave, wherein the second receiver is positioned on the rope further from the transmitter than the first receiver;
  (d) introducing an acoustic wave into the rope with the transmitter;
  (e) determining the time between the first signal generated by the first receiver and the second signal generated by the second receiver;
  (f) determining the velocity of the acoustic wave in the rope; and
  (g) calculating the residual strength of the rope.

* * * * *